United States Patent [19]
Bagrov

[11] Patent Number: 5,770,376
[45] Date of Patent: Jun. 23, 1998

[54] METHOD OF DIAGNOSING AND TREATING MYOCARDIAL INFARCTION AND HYPERTENSION

[75] Inventor: Alexei Y. Bagrov, St. Petersburg, Russian Federation

[73] Assignee: Biomedical Sciences Research Laboratories, Inc., Millersville, Md.

[21] Appl. No.: 396,487

[22] Filed: Mar. 2, 1995

Related U.S. Application Data

[63] Continuation-in-part of Ser. No. 181,918, Jan. 18, 1994, abandoned, which is a continuation-in-part of Ser. No. 984,480, Dec. 2, 1992, abandoned.

[51] Int. Cl.$^6$ ........................ G01N 33/53; G01N 33/536; G01N 33/74; G01N 37/00
[52] U.S. Cl. ........................ 435/7.1; 435/7.92; 435/7.93; 435/7.94; 435/7.95; 436/501; 436/536; 436/811; 436/817; 530/388.24; 530/388.25; 530/389.2; 530/389.3; 530/389.8; 530/388.9
[58] Field of Search ........................ 530/388.24, 388.25, 530/389.2, 389.3, 389.8, 388.9; 435/7.1, 7.92, 7.93, 7.94, 7.95; 436/501, 536, 811, 817

[56] References Cited

U.S. PATENT DOCUMENTS 5,117,834  6/1992  Kroll et al. .............................. 128/705
5,164,296  11/1992  Blaustein et al. ...................... 435/7.24

FOREIGN PATENT DOCUMENTS

WO 94/12210  6/1994  WIPO.

OTHER PUBLICATIONS

Anderson, D.E. & A.Bagrov, "Endogenous–Digoxin Like Factor (EDLF): Cardiovascular Responses to Volume Loading and pCO$_2$ Regulation," *J. Mol. Cell. Cardiol. 25(Suppl. I)*:S.22. Abstract II P 34 (1993).
Anderson, D.E. et al., "Inhibited Breathing Decreases Renal Sodium Excretion," *Psychosom. Med.* 57:373–380 (Jul.–Aug. 1995).
Bagrov, A.Y. et al., "Antiarrhythmic Effect of Antibodies to Digoxin in Acute Myocardial Ischemia in Rats," *Eur. J. Pharmacol.* 162:195–196 (1989).
Bagrov, A.Y. et al., "Antiarrhythmic Effect of Antibodies to Digoxin in Experimental Myocardial Infarction (the Arrhythmogenic Action of Endogenous Digoxinlike Factor)," pp. 919–921, translated from *Bull. Exp. Biol Med.* 112(7):20–21 (1991).
Bagrov, A. et al., "Digitalis–Like and Vasoconstrictor Properties of Endogenous Digoxin–Like Factor (EDLF) from Bufo Marinus Toad," *J. Mol. Cell. Cardiol.* 24(Suppl. I):S.259. Abstract P–08–30 (1992).
Bagrov, A.Y. et al., "Effect of Endogenous Digoxin Like Factor and Digoxin Antibody on Myocardial Na$^+$, K$^+$–Pump Activity and Ventricular Arrhythmias in Acute Myocardial Ischaemia in Rats," *Cardiovascular Res.* 27:001–006 (1993).

Bagrov, A.Y. et al., "Effects of Two Endogenous Na$^+$,K$^+$– ATPase Inhibitors, Marinobufagenin and Ouabain, on Isolated Rat Aorta," *Eur. J. Pharmacol. 00*:1–8 (1995).
Bagrov, A.Y. et al., "Endogenous Digitalis in Acute Myocardial Ischaemia/Infarction (AMI)," *Biol. Chem. Hoppe–Seyler* 374:610–611. Abstract SP–181 (1993).
Bagrov, A.Y. et al., "Endogenous Digoxin–Like Factor (EDLF) in Acute Myocardial Infarction (AMI)," *J. Mol. Cell. Cardiol.* 22(Suppl. III):S.29. Abstract PT4 (1990).
Bagrov, A. et al., "Endogenous Digoxin–Like Factor (EDLF): Pathophysiological Role in Acute Myocardial Ischaemia/Infarction (AMI)," *J. Mol. Cell. Cardiol* 25 (Suppl I):S.102. Abstract XI P 5 (1993).
Bagrov, A.Y. et al., "Endogenous Digoxin–Like Factor in Acute Myocardial Infarction," *J. Intern. Med.* 235(1):63–67 (1994).
Bagrov, A.Y., "Endogenous Digoxin–Like Factor: Possible Emergency Implications," *Prehosp. Disaster Med.* 5:186. Abstract (1990).
Bagrov, A.Y. et al., "Endogenous Marinobufagenin–Like Immunoreactive Factor and Na+, K+ ATPase Inhibition During Voluntary Hypoventilation," *Hypertension* 26(5):781–788. Abstract. (Nov. 1995).
Bagrov, A.Y. et al., "Endogenous Plasma Na,K–ATPase Inhibitory Activity and Digoxin Like Immunoreactivity After Acute Myocardial Infarction," *Cardiovascul. Res.* 25(5)371–377 (1991).
Bagrov, A. Y. et al., "Evidence for a Bufodienolide Na/K Pump Inhibitor in Human Urine," *Am. J. Hypertension* 9:133A–135A. Abstract D2 (1996).
Bagrov, A. Y. et al., "Marinobufagenin–Like Immunoreactive Substance, a Possible Endogenous Na,K–ATPase Inhibitor with Vasoconstrictor Activity," *Am. J Hypertension* 8(4):65A. Abstract C24 (Apr. 1995).

(List continued on next page.)

*Primary Examiner*—Ronald B. Schwadron
*Attorney, Agent, or Firm*—Sterne, Kessler, Goldstein & Fox P.L.L.C.

[57] ABSTRACT

The present invention relates to methods for diagnosing acute myocardial infarction through the measurement of the level of marinobufagin-like immunoreactivity in the blood of patients suspected of this diagnosis; a method for treating patients with acute myocardial infarction with antibody to marinobufagin, a bufodienolide, to prevent the occurrence of cardiac arrhythmias; antibodies which specifically recognize marinobufagin or other bufodienolides; hybridomas producing these antibodies; a process for preparing such antibodies; and an immunoassay method for marinobufagin for research purposes using its specific antibody.

The antibodies of the present invention make it possible to conveniently measure bufodienolides with specificity and high sensitivity. This is useful in determining the existence and degree of hypertension and myocardial infarction, and in treating myocardial infarction.

4 Claims, No Drawings

OTHER PUBLICATIONS

Bagrov, A. Y., et al., "Plasma Marinobufagenin–Like and Ouabain–Like Immunoreactivity During Saline Volume Expansion in Anesthetized Dogs," *Cardiovascular Res.* 31:296–305 (1996).

Blaustein, M.P., "The Cellular Basis of Cardiotonic Steroid Action," *Trends Pharmacol. Sci.* 6:289–292 (1985).

Bova, S. et al., "Effects of an Endogenous Ouabainlike Compound on Heart and Aorta," *Hypertension* 17(6):944–950 (1991).

Cloix, J.–F., "Endogenous Digitalislike Compounds: A Tentative Update of Chemical and Biological Studies," *Hypertension* 10(Suppl. 1):I–67–I–70 (1987).

Clough, D.L. et al., "Myocardial Na,K–ATPase Activity in Rats with Steroid and Spontaneous Hypertension," *J. Hypertension* 2(2):141–147 (1984).

De Mendonca, M. et al., "Hypotensive Action of Canrenone in a Model of Hypertension Where Ouabain–like Factors are Present," *J. Hypertension 3 (Suppl. 3)*:S73–S78 (1985).

de Pover, A., "Endogenous Digitalis–Like Factor and Inotropic Receptor Sites in Rat Heart," *Eur. J. Pharmacol.* 99:365–366 (1984).

Delva, P. et al., "Correlations Between Plasma Levels of an Endogenous Digitalis–Like Substance and Haemodynamic Parameters Measured During Cardiac Catheterization," *J. Hypertension 6(Suppl. 4)*:S–348 to S–350 (1988).

Doris, P.A. and D.M. Stocco, "An Endogenous Digitalis–Like Factor Derived from the Adrenal Gland: Studies of Adrenal Tissue from Various Sources," *Endocrinology* 125(5):2573–2579 (1989).

Fagoo, M. and T. Godfraind, "Interaction of Cardiodigin, Endogenous Inhibitor of $Na^+$, $K^+$–ATPase, with Antidigoxin and Antidigitoxin Antibodies," *Biochem. Biophys. Res. Commun.* 129(2):553–559 (1985).

Fedorova, O.V. and A.Y. Bagrov, "Inhibition of Na/K ATPase from Rat Aorta by Two Endogenous Na–Pump Inhibitors, Ouabain and Marinobufagenin," *Am. J. Hypertension* 9(4):23A. Abstract (Apr. 1996).

Flier, J.S., "Ouabain–Like Activity in Toad Skin and Its Implications for Endogenous Regulation of Ion Transport," *Nature* 274:285–286 (1978).

Gonick, H.C. et al., "Circulating Inhibitor of Sodium–Potassium–Activated Adenosine Triphosphatase After Expansion of Extracellular Fluid Volume in Rats," *Clin. Sci. Mol. Med.* 53:329–334 (1977).

Goodlin, R.C., "Antidigoxin Antibodies in Eclampsia," *N. Engl. J. Med.* 318:518–519 (1988).

Graves, S.W., "The Possible Role of Digitalislike Factors in Pregnancy–Induced Hypertension," *Hypertension 10(Suppl. I)*:I–84–I–86 (1987).

Hamlyn, J.M. et al., "A Circulating Inhibitor of ($Na^+ + K^+$)ATPase Associated with Essential Hypertension," *Nature* 300:650–652 (1982).

Harris, D. W. et al., "Development of an Immunoassay for Endogenous Digilitalislike Factor," *Hypertension* 17(6), Part 2:936–943 (1991).

Harris, W.J. and S. Emery, "Therapeutic Antibodies—the Coming of Age," *Trends in Biotechnol.* 11:42–44 (1993).

Harrison, T.R., "Specific Disorders of Rate and Rhythm," *Harrison's Principles of Internal Medicine,* Ninth Edition, Chapter 237, pp. 1051–1063, Isselbacher, K.J. et al., eds., McGraw–Hill Book Company, New York, 1980.

Huang, C.T. and R.M. Smith, "Lowering of Blood Pressure in Chronic Aortic Coarctate Hypertensive Rats with Anti–Digoxin Antiserum," *Life Sci.* 35:115–118 (1984).

Janse, M.J. and A.L. Wit, "Electrophysiological Mechanisms of Ventricular Arrhythmias Resulting From Myocardial Ischemia and Infarction," *Am. Physiolog. Rev.* 69(4):1049 & 1058–1061 (1989).

Kohn, R. et al., "Endogenous Digitalis–Like Factor in Patients with Acute Myocardial Infarction," *Cor et Vasa.* 34(3):227–237. Abstract. (1992).

Kojima et al., "Involvement of Endogenous Digitilas–Like Substance in Genesis of Deoxycorticosterone–Salt Hypertension," *Life Sci.* 30:1775–1781 (1982).

Kuneš, J. et al., "The Importance of Endogenous Digoxin–Like Factors in Rats with Various Forms of Experimental Hypertension," *Clin. and Exper.—Theory and Practice A7(5&6)*:707–720 (1985).

Lichtstein, D. et al, "Demonstration of a Ouabainlike Plasma Compound in Hypertension Prone and Hypertension Resistant Rats," *Hypertension* 7(5):729–733 (1985).

Ludens, J.H. et al., "Purification of an Endogenous Digitalislike Factor From Human Plasma for Structural Analysis," *Hypertension* 17(6), Part 2:923–929 (1991).

Mir, M.A. et al., "Problems and Pitfalls in the Isolation of an Endogenous $Na^+,K^+$–ATPase Inhibitor," *Hypertension* 10(5)(Suppl. 1):I–57–I60 (1987).

Schoner, W., "Endogenous Digitalis–Like Factors," *Clin. Exp. Hypertension—Theory and Practice A14(5)*:767–814 (1992).

Schreiber, V. et al., "Digoxin–like Immunoreactivity in the Serum of Rats with Cardiac Overload," *J. Mol. Cell. Cardiol.* 13:107–110 (1981).

Shimada, K. et al., "Structure–Activity Relationship of Bufotoxins and Related Comopunds for the Inhibition of $Na^+,K^+$–Adenosine Triphosphatase," *J. Pharmacobio–Dyn.* 8:1054–1059 (1985).

Shimada, K. et al., "Occurrence of Bufadienolides in the Skin of *Bufo viridis* LAUR." *Chem. Pharm. Bull.* 34(8):3454–3457 (1986).

Waldmann, T.A., "Monoclonal Antibodies in Diagnosis and Therapy," *Science* 252:1657–1662 (1991).

Wenwu, Z. et al., "Serum Endogenous Digitalis Like Factor in Acute Myocardial Infarction Patients," *Proceedings of the Second International Urban Emergency Medicine Symposium*:56 (1993).

Yamahara, J. et al., "The Mode of Cardiac Action of Cardiotonic Steroids Isolated from Toad Cake in Perfused Working Guinea–Pig Heart and Effect of Cinobufagin on Experimental Heart Failure," *Nippon Yakurigaku Zasshi* 88:413–423 (1986).

Seaver, Gen. Eng. News, 14: 10, 21, 1994.

Bagrou et al., Eur. J. Pharma., 234: 165–172, 1993.

5,770,376

METHOD OF DIAGNOSING AND TREATING MYOCARDIAL INFARCTION AND HYPERTENSION

This application is a continuation-in-part of U.S. application Ser. No. 08/181,918, filed Jan. 18, 1994, now abandoned, which is a continuation-in-part of U.S. application Ser. No. 07/984,480, filed Dec. 2, 1992, now abandoned.

FIELD OF THE INVENTION

The present invention relates to methods for diagnosing and treating myocardial infarction and hypertension using an antibody which specifically recognizes marinobufagin-like immunoreactivity, methods for assaying marinobufagin and other bufodienolides for research purposes using antibodies, hybridomas producing these antibodies, a process for preparing the antibodies, and

BACKGROUND OF THE INVENTION

Hypertension is the primary risk factor for coronary, cerebral and renal vascular diseases which cause over half of all deaths in the United States. It has been estimated that the number of hypertensive patients in the United States alone is substantially 57 million and on the rise. The widespread awareness of the danger of elevated blood pressure has become the most frequent reason for visits to physicians. No single or specific cause is known for the hypertension referred to as primary (essential) hypertension. Primary hypertension has been attributed to such causes as hemodynamic pattern, genetic predisposition, vascular hypertrophy, hyperinsulinemia, defects in cell transport or binding, defects in the reninangiotensin system (low-renin or high renin hypertension) and along with insulin, angiotensin and natriuretic hormone, catecholamines arising in response to stress are known to be pressor-growth promoters. Increased sympathetic nervous activity may raise the blood pressure in a number of ways, for example, either alone or in concert with stimulation of renin release by catecholamines, causing arteriolar and venous constriction, by increasing cardiac output, or by altering the normal renal pressure-volume relationship. Primary hypertension is also associated with, for example, obesity, sleep apnea, physical inactivity, alcohol intake, smoking, diabetes mellitus, polycythemia and gout. Secondary forms of hypertension may arise from oral contraceptive use and parenchymal renal disease: renovascular hypertension caused by, for example, atherosclerotic disease, tumors (renin-secretory tumors); Cushing's Syndrome; heart surgery; and pregnancy. Chronic hypertension and renal disease during pregnancy may progress into eclampsia, a primary cause of fetal death.

It has been theorized that blood serum and various mammalian tissues contain a substance, biologically and immunoreactively, similar to digitalis glycosides and digoxin (ouabain)-like which have been labeled endogenous digoxin-like factors (EDLF). This theory has been supported in recent years by considerable evidence of a causal role for sodium in the genesis of hypertension. The evidence includes the finding of increased intracellular sodium in hypertensive mammals. Increases have also been noted in normotensive children of hypertensive parents. It has been discovered that an increased fluid volume stimulates the secretion of EDLF that inhibits the Na+,K+-ATPase pump. The inhibition is brought about by the reaction of the EDLF with the alpha-subunit of the ouabain-sensitive-magnesium-dependent, Na+,K+-ATPase in a manner similar to the digitalis glycosides. In the case of renovascular types of hypertension, inhibition of the sodium pump increases renal sodium excretion and restores vascular volume while at the same time leading to hypertension by increasing intracellular sodium content by potentiating preexisting vasoconstriction and finally initiating a new circle in the pathogenesis of hypertension. Increased plasma concentrations of EDLF have been discovered in hypertension caused by other physical and pathological conditions. Consequently, it was discovered that the administration of an antidigoxin antiserum to hypertensive animals causes a pronounced decrease in the blood pressure.

The exact chemical nature, as well as the site of origin, of EDLF is not known. It has been proposed that endogenous digoxin is a peptide originating in the hypothalamus. It has also been reported that EDLF originates in the adrenals and the heart. It has been shown that the EDLF substance exists in several different molecular forms, at least one of the forms being steroidal in nature. Confirming this, it was discovered that several steroids with digitalis-like imnunoreactivity and ability to inhibit Na+,K+-ATPase were identified in various amphibian tissues.

It was discovered that EDLF has direct effects on the heart and that the mammalian heart contains a substance with digoxin-like immunoreactivity and other properties of digitalis. The existence of the different subpopulation of the high-affinity receptors for digitalis in myocardium and neural endings in the heart indicated the existence of an endogenous ligand(s) at these receptor sites. It is known that an overdose of digitalis glycosides provokes cardiac arrhythmias, including ventricular tachycardia and ventricular fibrillation, rather than increasing cardiac contractility. Acute myocardial ischemia (AMI) sensitizes the myocardium to the arrhythmogenic effect of digitalis and is associated with both the inhibition of myocardial sodium pump activity and with the loss of digitalis specific receptors. Based upon this prior knowledge, it was hypothesized that the increased plasma concentrations of EDLF contributed to the origin of the hypersensitivity of the ischemic myocardium to digitalis and that EDLF participates in the genesis of myocardial ischemia-induced arrhythmias. Based upon this hypothesis, it was discovered that the plasma concentration of digoxin-like immunoreactivity, (for example) EDLF, was significantly increased after a first transmural myocardial infarction. It was further discovered that acute myocardial ischemia is associated with a marked increase in the concentration of EDLF, which increase occurs in parallel with the onset of ventricular arrhythmias.

BRIEF DESCRIPTION OF THE INVENTION

The present invention relates to (1) an antibody reacting specifically to marinobufagin, a bufodienolide, (2) antibodies to other bufodienolides, (3) hybridomas for producing such antibodies, (4) a process for preparing such antibodies, (5) a method for measuring marinobufagin-like immunoreactivity which comprises using such an antibody, (6) a method for diagnosing hypertension using such an antibody, (7) a method for diagnosing myocardial infarction and the risk of cardiac arrhythmias using such an antibody, and (8) a method of treating myocardial infarction using such an antibody.

DETAILED DESCRIPTION OF THE INVENTION

When this work began, crude venom from the parotid glands of the *Bufo marinus* toad was used. Liquid venom was obtained by gently pressing on the skin around the glands. About twenty four hours after the liquid venom was obtained it crystallized at room temperature. The *Bufo marinus* venom was compared with the effects of bufalin obtained from Sigma (0.1–50 mm). The testing was carried out on isolated abdominal aortic strips obtained from adult male Wistar rats. The animals were sacrificed by exsanguination. Rings of the abdominal aorta (1–1.5 mm diameter) were excised proximal to the origin of the renal arteries and suspended in a 10.0 ml bath perfused by 32° C. Tyrode solution bubbled by a mixture of 95% $O_2$ and 5% $CO_2$ under resting tension of 1 gram. Contractions of the aortic strip were recorded isometrically using a force transducer and displayed on a pen oscillograph. After a 60 minute equilibration period, dose-response curves to the vasoconstrictor effect (aortic strips) of the venom were plotted in the absence, and in the presence, of various pharmacological agents.

At concentrations of 0.3–10 ug/ml (n=9 for each described experiment) crude *Bufo marinus* venom possessed a dose-dependent vasoconstrictor response. Vasoconstrictor response to the venom was unaffected by alpha- and beta-adrenergic antagonists, 5-HT antagonists and calcium channel blockers. Addition of antidigoxin antibody to the incubation medium significantly reduced the vasoconstrictor response, while in vitro preinoculation of the venom with the antidigoxin antibody for twenty minutes completely prevented the vasopressor effect.

DIGIBIND, Fab fragments of bovine antidigoxin antibody (Burroughs Wellcome Co.), at concentrations up to 40.0 mg/ml had no effect on the vasoconstrictor effects of the venom. Bufalin at concentrations of 0.1–10 $\mu$M/l displayed weak and delayed vasoconstriction.

It was concluded that (1) The digitalis-like compound(s) contained in the venom from the parotid glands of the *Bufo marinus* toad, unlike previous candidates for the role of endogenous digitalis (EDLF), possess significant in vitro vasoconstrictor activity. These vasoconstrictor effects were blocked by antidigoxin antibody. (2) DIGIBIND, Fab fragments of bovine antidigoxin antibody, is absolutely ineffective in blocking the action of EDLF from the toad venom. (3) Since antidigoxin immunoglobulin G recognized and antagonized EDLF, but DIGIBIND, Fab fragments of bovine antidigoxin antibody, failed to bind EDLF: EDLF has immunoreactions different from digoxin. We hypothesized from the foregoing that antibody raised against EDLF should recognize EDLF better than antidigoxin antibody. As mentioned, *Bufo marinus* venom possessed significant vasopressor activity. As shown in the art the venom contains a mixture of several steroids.

To carry the experimentation further, *Bufo marinus* toad poison was collected from the parotid glands of five adult spades of both sexes of the toad. Following crystallization at 37° F. for twenty four hours, 800 mg of the poison was extracted in 5.0% ethanol for about two weeks with periodic shaking. The ethanol extract was filtered and the sediment was further washed with 3 ml of 50% ethanol. For further extraction of the steroids, equal volumes of the ethanol solution was diluted 1:1 with distilled chloroform. The mixture was then centrifuged in order to obtain chloroform and ethanol phases. The chloroform phase was isolated and another portion of distilled chloroform was added. The procedure was repeated two times after which the chloroform phases were mixed and vacuum distilled. A dark brown oily residue was obtained and dissolved in 1 ml of concentrated ethyl ether in acetic acid. The non-dissolvable portion of the residue was separated by filtration. A mixture of steroids was separated by thin-layer chromatography. Ethyl acetate was used as the eluent.

Rat aortic rings were treated by the mixture of steroids (0.1–5 ug/kg) in six experiments. The blood vessels were constricted in a dose dependent manner. The vasoconstriction effect of the mixture of steroids was unaffected by the adrenergic blockade of 2 $\mu$M phentolamine. Accordingly, it was concluded that the vasoconstrictor effect of the venom was due to the presence of the steroidal substance(s).

The steroids in the venom were then identified using UV. A spot corresponding to marinobufagin was scraped, divided into three portions and extracted with ethyl acetate. In a parallel manner all of the spots corresponding to the steroids present were extracted with ethyl acetate. The spots yielded, in addition to marinobufagin, resibufagenin, substance L, bufalin, telocinobufagin, argentinoginin, jamaicogenin, gellerbrigenol, gamabufotalin and substance D.

The compounds were each studied for their ability to contract isolated rat aorta (n=4) in each series. Only the fraction of marinobufagin showed rapid and strong vasoconstrictor effects insensitive to adrenergic blockers.

The major constituent of the *Bufo marinus* toad venom (7.9% of the total venom weight) is marinobufagin. The second major constituent of the venom is bufalin (0.48%) which compound did not show any intrinsic vasoconstrictor activity. The third and fourth major steroids present were telocinobufagin (0.06%) and resibufagenin (0.04%) which were in such low concentrations that neither was able to produce any results. It is therefore concluded that the vasoconstrictor action was attributable solely to the marinobufagin.

From the examples set out hereinafter taken with the foregoing it was concluded that marinobufagin is an EDLF in mammals as well as rats. It is also shown that anti-marinobufagin antibody utilized in acute myocardial ischemia in rats suppressed arrythmias better than anti-digoxin antibody. Moreover, in patients with acute myocardial infarctions, an ELISHA immunoassay based on anti-marinobufagin antibody allowed one to detect plasma levels of marinobufagin to orders of the highest magnitude as compared with digoxin immunoassay. It was further determined that the ELISA marinobufagin assay allowed one to detect plasma levels of marinobufagin exactly corresponding to the ability of marinobufagin to inhibit Na,K-ATPase.

It was unexpectedly discovered that the antibody prepared from marinobufagin prevented the effects of increased plasma concentrations of EDLF, for example arrhythmias, and prevented hypertension. The invention enabled a method of diagnosis and of predicting the onset of cardiac arrhythmias caused by various pathological conditions. It was previously discovered that antibodies prepared from the steroid compounds derived from marinobufagin effectively blocked endogenous digoxin-like factors found in the plasma of man.

Treatment to prevent or alleviate cardiac arrhythmias utilizing the antibody of the invention may be by any of the conventional routes of administration, for example, oral, intramuscular, intravenous or rectally. In the preferred embodiment, the antibody is administered in combination with a pharmaceutically-acceptable carrier which may be solid or liquid, dependent upon choice and route of administration. Examples of acceptable carriers include, but are not limited to, for example, physiological saline solution.

In the preferred embodiment, the inventive compounds are administered intravenously. The actual dosage unit will be determined by such generally recognized factors as body weight of patient and the severity and type of pathological condition the patient might be suffering from. With these considerations in mind, the dosage of a particular patient can be readily determined by the medical practitioner in accordance with the techniques known in the medical arts.

EXAMPLE 1

Purification and Characterization of Marinobufagin.

The *Bufo marinus* toad poison used in the examples was obtained from venom obtained from the parotid glands of *Bufo marinus* male and female adult toads obtained from the St. Petersburg, Russia and Riga, Latvia Zoological Gardens. The venom was extracted by gently pressing on the skin around the glands. The venom crystallizes at room temperature within 24 hours. We extracted 800 mg of the crystallized poison using 50% ethanol at a temperature of 30° C. over a two-week period.

Following the alcoholic extraction, the mixture was filtered through Shott Nr 4 filters. The filtrand was divided into two portions. Each portion was washed with 3 ml 30% ethanol. After removal of the filtrate the residue was further extracted with a 1:1 solution of 50% ethanol and chloroform followed by centrifugation in order to obtain chloroform and ethanol phases. The chloroform phases were isolated and extracted by centrifugation repeated two times after which the chloroform phases were mixed and distilled under vacuum. A dark brown oily residue resulted which was dissolved in 1 ml of ethyl acetate. The non-soluble residue was separated by filtration.

A mixture of steroid compounds was obtained and separated by thin-layer chromatography (Silufol VV 254, Sigma Chemicals), plates were pre-exposed to 1 hour preincubation at 100° C. Ethyl acetate was used as the eluent. Identification of the individual steroids was performed by UV. A spot corresponding to marinobufagin (Mbg) was scraped, divided into three (3) portions and extracted with ethyl acetate. In parallel series all eleven (11) spots corresponded to the steroids resibufagenin, substance L, bufalin, marinobufagin, telocinobufagin, argentinogenin, gellerbrigenin, jamaicogenin, gellerbrigenol, gamabufotalin, and substance D.

Detection of marinobufagin and other bufosteroids was accomplished by (a) visualization under ultraviolet (UV) light and comparison of chromatographic mobility, (b) spraying a saturated chloroform solution of $SbCl_3$ for color reactions, and (c) UV absorbance characteristics that are typical for marinobufagin (=300 nM, E=18600).

The other steroid compounds and substances were scraped from the Silufol plates and treated by the same procedure as the marinobufagin. The steroids developed and used in the experiments herein are as follows:
1. Resibufagenin, 3 beta hydroxy 14,15 epoxybufodienolide
2. Marinobufagin, 3 beta, 5 beta dihydroxy 14,15 epoxybufodienolide
3. Cinobufagin, 3 beta 16 beta acetoxy 14,15 epoxybufodienolide
4. Bufalin, 3 beta 14 beta dihyroxybufodienolide
5. Telocinobufagin, 3 beta 5 beta 14 beta trihydroxybufodienolide
6. Gamabufotalin, 3 beta 11 beta 14 beta trihydroxybufodienolide
7. Gellerbrigenin, 3 beta 5 beta 14 beta trihydroxy 19 nor-19 aldehyde bufodienolide

EXAMPLE 2

Synthesis of Antibodies to Marinobufagin

In order to become immunogenic, marinobufagin must first be conjugated with a sugar residue in order to further conjugate it with BSA.

We dissolved 50 mg of marinobufagin (purified by thin layer chromatography) in 10 ml of absolute dry benzene. Then 80 mg of $Ag_2CO_3$ was added to the solution. The solution was then heated to boiling, and, while stirring, a solution of 180 mg of acetobromo-D-glucose in 15 ml of dry benzene was added by drops to the marinobufagin solution. The reaction was controlled by thin-layer chromatography on silicagel; disappearance of the spot corresponding to marinobufagin showing that conjugation of marinobufagin with glucose was successful. After the reaction was finished the silver salt was filtered and the filtrand was evaporated. The compound was dissolved in ether; the nondissolvable residue was filtered; and the glycoside was crystallized from the filtrand.

Conjugation of marinobufagin-glycoside with bovine serum albumin (BSA) was performed as described by Curd et al for digoxin.

Prior to the immunization, the conjugate Mbg-glycoside-BSA was further compared with Mbg for its ability to react with polyclonal antidigoxin rabbit antibody from the DELFIA immunoassay. In the DELFIA assay equimolar concentrations of Mbg and its conjugate demonstrated exactly similar displacement of digoxin standards. Therefore, the conjugation procedure did not alter the immunoreactive properties of the antigen.

Immunization and Development of Antibodies

The polyclonal antimarinobufagin antibody of the invention was obtained by immunizing chinchilla rabbits with a marinobufagin-3-glycoside-bovine serum albumin conjugate. Each animal was injected with 0.5 mg of the conjugate dissolved in 0.5 ml water and mixed in a ratio of 1:1 with Freund's adjuvant. The mixture was administered by subcutaneous injection in five different locations on the backs of the rabbits over a four-week period.

Serum was obtained from the rabbits and the inventive immunoglobulins were separated from the whole serum in the following steps:

Step 1. The serum was diluted (1:4) with an acetate buffer (60 mM $CH_3COONa$—$CH_3COOH$, pH 4). The pH of the solution was adjusted to pH 4.5 using O0.1 N NaOH.

Step 2. We slowly added 25 NL Caprylic (octanoic) acid with stirring to 1 ml of the serum solution. The final solution was stirred for thirty (30) minutes followed by centrifuging to separate proteins of non-immunoglobulin nature.

Step 3. The supernatant from Step 2 was filtered and the filtrate was dissolved, 9:1, in a phosphate buffer solution (150 mM NaCl, 3 mM KCl, 8 mM $Na_2HPO_4$, 1.5 mM $KH_2PO_4$, pH 7.2). The pH was adjusted to 7.4 with 1N NaOH. The resulting solution was cooled to 40° C. followed by the addition of $NH_4OH$. The resulting mixture was centrifuged and a precipitate of proteins separated.

Step 4. The precipitate from Step 3 was dissolved in the minimal amount of distilled water and dialyzed in separate dialysis bags (threshold, protein with m.w. 17,000 D) against two changes of 1 liter of distilled water. Dialysis was controlled by concentrated $BaCl_2$ (in the presence of the $SO_4$ ions we saw undissolvable $BaCl_2$). The dialyzed anti-Mbg immunoglobulin of the invention obtained hereby was used in the tests.

EXAMPLE 3

Characterization of the Antibody

Immunoassay-ELISA

The test of cross-immunoreactivity was defined as the ratio: Amount of Mbg required to displace 50% of maximally bound Mbg from antiMbg antibody:Amount of the cross-reactant to give the same 50% displacement $$\frac{\text{Amount of } Mbg \text{ required to displace 50\%}}{\text{Amount of the cross-reactant to give the same}}$$
of maximally bound $Mbg$ from anti$Mbg$ antibody
50% displacement Calibration curve of the ELISA assay (average of 5 experiments):

| Conc. of antigen ($Mbg$) | 0 | $5 \times 10^{-9}$ | $5 \times 10^{-8}$ | $5 \times 10^{-7}$ | $5 \times 10^{-6}$ | $5 \times 10^{-5}$ |
|---|---|---|---|---|---|---|
| Inhibition of the binding of antibody with $Mbg$ | 0 | 10 | 17 | 22.5 | 45 | 74.5 |

Mbg content in blood serum and tissue was assayed using half area enzyme immunoassay plates coated with BSA (bovine serum albumin) marinobufagin by adding to each well 50–100 µl of 1 ng/ml BSA-Mbg in a buffer (50 mM sodium carbonate, pH 8.6). The plates were stored at 4° C. for 1–2 days. Unbound BSA-Mbg conjugate was washed out by washing each well repetitively with rinse solution (0.09% NaCl) containing 0.05% TWEEN 20 (polyoxyethylenesorbitan monolaurate).

The titer of anti-Mbg antibody from immunized rabbits or produced by the hybridoma technique was determined on plates as described above. Doubling dilutions of antibody were added to the wells starting from 1:1000. The plates were incubated with shaking for 60 minutes at a temperature of 30° C.; this allows the anti-Mbg antibody to bind to the BSA-Mbg conjugate attached to a plate. After incubation, the antibody was washed out with four rinses. Antibody which bonded to Mbg remained attached to the wells. Then 1:1,000 dilutions of goat anti-rabbit IgG horseradish peroxidase conjugate were added to each well for 60 minutes with continuous shaking. The unbound goat anti-rabbit IgG-peroxidase conjugate was then washed away. Then TMB reagent was added (50 µl to each well). After 15 minutes the reaction was stopped by addition of 50 µl of 1M $H_3PO_4$.

The absorbance of each well was measured at 450 nm. A standard Mbg (marinobufagin) curve was plotted (0.1 to 10000 nM/1). Addition of Mbg prevents binding of anti-Mbg antibody to BSA-Mbg conjugate in the well. Consequently, less goat anti-rabbit IgG binds to the well and we see less absorbance at 450 nm.

In our experiments cross-reactivity of the anti-Mbg antibody with ouabain, ouabagenin and bufalin was less than 1%. Cross-reactivity with digoxin, digitoxin, digoxigenin, and digitoxigenin was less than 10%.

It will be understood by those skilled in the art that other methods of immunoassay are readily available in the art, for example, radioimmunoassay.

Immunoassay-2, Fluoroimmunoassay

Marinobufagin-like immunoreactivity was measured using a solid-phase fluoroimmunoassay. The method is based on competition between the immobilized conjugate (marinobufagin-3-glycoside-RNAase, 19:1) and a rabbit polyclonal antimarinobufagin antibody. Marinobufagin-3-glycoside-RNAase conjugate was prepared, and rabbits were immunized with marinobufagin-3-glycoside-BSA, as previously reported by Curd et al for digoxin. Marinobufagin-3-glycoside-RNAase conjugate (1.0 µg of conjugate in 100 µl of phosphate buffered saline per well) was immobilized on the bottom of NANC microtitration strip wells as reported in detail previously by Helsingius et al. We added 40 µl of marinobufagin standards and unknown samples to the coated wells, followed by 100 µl of marinobufagin antibody. After one hour incubation, the strips were washed twice (DELFIA wash solution, Wallac Oy, Turku, Finland), following which 100 µl of secondary antibody (europium-labeled goat anti-rabbit antibody, Wallac Oy, Turku, Finland) was added. After one hour incubation, the wells were washed six times with the wash solution. Then, 200 µl of enhancement solution, which releases the europium conjugated with the secondary antibody, (Wallac Oy, Turku, Finland) was added to each well, the strips were shaken for 5 minutes, and after 10 minutes more the fluorescence of free europium was measured (DELFIA 1234 Arcus Fluorometer, Wallac Oy, Turku, Finland). The sensitivity of the immunoassay was 0.001 nmol. Cross immunoreactivity of the assay was expressed as the ratio of the amount of cross-reactant required to displace 50% of antimarinobufagin, antiouabain or antidigoxin antibody from immobilized conjugate to the amount of the cross-reactant to give the same 50% displacement. Cross-reactivity of antimarinobufagin antibody with digoxin, ouabain, digitoxin bufalin, cinobufagin, mixture of bufosteroids from *Bufo marinus* toad excluding marinobufagin, prednisone, spironolactone, proscillaridine, progesterone and 5-beta cholanic acid was 0.1%, <0.01%, 3%, 1%, 0.1%, 5%, <0.1%, <0.1%, 1%, <0.5% and 1%, respectively.

EXAMPLE 4

Preparation of Hybridoma

The monoclonal antibody of the invention is prepared by emulsifying about 1–5 mg/ml of Mbg-BSA conjugate in saline solution with Freund's complete adjuvant 1:1. Emulsification can be readily carried out by repeatedly squirting the suspension through the nozzle of a syringe. A total dosage of about 0.3 ml is injected into multiple sites in mice, for example, in the legs and at the base of the tail. Injections are repeated at intervals of three to five weeks. Approximately ten days after each treatment, a drop of blood is taken from the tail of each mouse. The extracted blood is tested for the presence of specific antibodies. The animals yielding the best antiserum are selected for fusion.

After a rest period of at least one month, 0.2–0.4 ml of the Mbg-BSA conjugate solution, without Freund's adjuvant, is injected intravenously into each mouse. The injected mice are sacrificed 3–4 days later and the spleens removed under sterile conditions. The spleens are placed into a petri dish containing about 5 ml of 2.5% FCS-DMM kept on ice and washed gently. The spleens are then transferred to a round-bottomed tube, cutting them into three or four pieces per spleen, with about 5 ml of fresh 2.5% FCS-DMM. Using a Teflon pestle, the pieces are squashed gently to make cell suspensions. The clumps and pieces of connective tissues are allowed to sediment, then the cell suspensions are transferred to round-bottomed tubes. The tubes are filled with 2.5% FCS-DMM and spun at room temperature for 7–10 minutes at 400 g. The pellets are resuspended in about 10 ml of fresh medium and centrifuged as above. The pellets are then resuspended in 10 ml of medium, and the cells counted. Viability at this point should be higher than 80%.

Enough myeloma cells from a culture in logarithmic growth are pelleted by centrifugation at room temperature for 10 minutes at 400 g. The pellets are resuspended in 10 ml of 2.5% FCS-DMM and counted. Although the fusion and the initial selection of hybrids by growth in HAT medium are quite distinct stages, for convenience they are described together. For convenience, the fusion of cells in suspension is being described as by the spleens. The Mbg/spleen cells and the myeloma cells are prepared as above. About $10^8$ spleen cells and $10^7$ myeloma cells are mixed. DMM is added to a volume of 50 ml. The cells are spun down at room temperature for 8 minutes at about 400 g. The supernatant is removed with a Pasteur pipette connected to a vacuum line. Complete removal of the supernatant is essential to avoid dilution of the PEG (polyethylene glycol solution). The pellet is broken by gently tapping the bottom of the tube. The tube is placed in a 200-ml beaker containing water at 40° C. and maintained there during the fusion.

We add 0.8 ml of 50% PEG prewarmed to 40° C. to the pellet using a 1-ml pipette, over a period of 1 minute, continuously stirring the cells with the pipette tip. Stirring of the cells in 50% PEG is continued for a further 1.5 minutes. Agglutination of the cells is evident. With the same pipette, 1 ml of DMM is added, taken from a tube containing 10 ml of DMM kept at 37° C., to the fusion mixture, continuously stirring as before, over a period of 1 minute. The preceding step is repeated and then repeated twice adding the medium in 30 seconds. Using the same pipette with continuous stirring, the rest of the 10 ml of DMM is added over a period of about 2 minutes. With a 10 ml pipette, 12–13 ml of prewarmed DMM is added and the mixture spun down for about 8 minutes at 400 g. The supernatant is discarded and the pellet gently broken up by tapping the bottom of the tube and suspended in approximately 49 ml of 20% FCS-DMM.

This fusion suspension is distributed in the 48 wells of two Linbro plates. With a further 1 ml of 20% FCS-DMM $10^8$ spleen cells/ml are added to the wells. The wells are incubated overnight at 37° C. in a $CO_2$ incubator. Using a Pasteur pipette connected to a vacuum line, 1 ml of the culture medium is removed from each well without disturbing the cells. The plate is fed with a 1 ml HAT medium for 2–3 days afterwards until a vigorous growth of hybrids is evident under the microscope. The culture becomes more yellow and may be tested for antibody activity. Duplicates of the growing hybrid cultures, either all or selected ones, are prepared and fed for a week with HAT medium.

EXAMPLE 5

Effects of Antibodies During Acute Myocardial Ischemia in Rats

Acute myocardial ischemia was set up in seventy-three adult male Wistar rats anesthetized with sodium pentobarbital (75 mg/kg intramuscularly) and artificially ventilated via tracheostomy. After thoracotomy, the left coronary arteries were ligated 1–2 mm distal to their origins. The hearts were monitored by three standard ECG leads. Test drugs were administered into the femoral veins via polyethylene catheters. After fifteen minutes of acute myocardial ischemia, the animals were sacrificed by exsanguination. It will be understood by those skilled in the art that the fifteen minute period corresponds to an approximate three to four hour period of myocardial infarction in humans. Blood samples were collected from the abdominal aortas into cooled polyethylene tubes containing 0.1 M EDTA and 10 $\mu$M phenylmethylsulfonylfluoride (50 $\mu$l per 4 ml blood). The resulting solution was frozen at -20° C. for determination of digoxin-like immunoreactivity (DLIR) in the plasma. The digoxin-like immunoreactivity was measured using dissociation enhanced lanthanide fluoroimmunoassay (DELFIA) kits by LKB, Finland. This assay of digoxin is a solid phase immunoassay based on competition between immobilized digoxin and sample digoxin (in the present case, EDLF) for europium-labeled polyclonal antidigoxin antibodies derived from rabbits. Standard and sample (or EDLF) reduce the binding of the europium labeled antibodies to the immobilized digoxin molecules. Finally fluorescence in the strip wells is measured in a resolved time result LKB-Wallac fluorometer. Plasma levels of marinobufagin-like immunoreactivity (MLIR) were measured as mentioned above in Example 3.

Arrhythmia incidence was defined as the total duration of ventricular tachycardia (VT) and ventricular fibrillation (VF) during the fifteen minute postligation period. The animals were divided into five groups as follows:

Group 1. Twelve (12) control, rats subjected only to thoracotomy;

Group 2. Twenty-eight (28) rats pretreated with an intravenous injection of 0.2 ml isotonic saline prior to the period of acute myocardial ischemia;

Group 3. Fifteen (15) rats pretreated by intravenous injection of 260 ug/kg antidigoxin immunoglobulin;

Group 4. Five (5) rats pretreated by intravenous injection with 5 mg/kg DIGIBIND (Fab fragments of bovine antidigoxin antibody, a drug produced for the treatment of digoxin overdose by Burroughs Wellcome Co.); and Group 5. Seven (7) rats pretreated with 40 mg/kg DIGIBIND, Fab fragments of bovine antidigoxin antibody, Group 6. Ten rats pretreated with antimarinobufagin antibody (250 ug/kg).

All pretreatment of the animals was carried out thirty minutes prior to coronary ligation. The control animals were pretreated thirty minutes prior to thoracotomy.

No heart rhythm disturbances were observed in the control animals. The plasma concentration of DLIR in the control animals was 0.48±0.09 ng/ml. Acute coronary ligation in Group 2 (ischemia without treatment) animals resulted in typical ischemic changes of the ECG, i.e., increase in the R wave, elevation of the ST-T segment and in the onset of ventricular arrhythmias. Average duration of VT and VF in Group 2 was 201±31 sec. Plasma concentration of DLIR 15 minutes post coronary artery ligation was 1.13±0.32 ng/ml, p<0.05. In the (Group 2) rats with acute myocardial ischemia the plasma concentration of MLIR was 3±0.5 $\mu$M/l 15 minutes after the coronary ligation as compared with 0.3±0.05 $\mu$M/l in the control group (which was the same as in intact rats without thoracotomy).

The Group 3 animals (pretreated with antidigoxin IgG) exhibited a reduced average duration of VT and VF to 46±18 sec. (p<0.01) The Group 4 animals (pretreated with DIGIBIND, Fab fragments of bovine antidigoxin antibody,) did not exhibit any change in the incidence of post-ligation arrhythmias.

The average duration of VT and VF was reduced to 74±34 sec in the Group 5 (pretreated with high-dose DIGIBIND, Fab fragments of bovine antidigoxin antibody, animals. This difference was not statistically significant when compared with the Group 1 (untreated) animals with myocardial ischemia.

The average duration of VT and VF in 10 rats pretreated with antimarinobufagin antibody (Group 6) was the lowest, 18.7±6.5 sec.

From this experiment, it was concluded:

1. Acute myocardial ischemia in rats is associated with an increase of the concentration of digoxin-like immunoreactivity and a more marked increase in Mbg-like immunoreactivity. This indicates that MLIR is a marker for acute myocardial infarction.
2. The increase in digoxin-like and Mbg-like immunoreactivity occurs in parallel with the onset of ventricular arrhythmias. This suggests that increasing levels of EDLF (or specifically, Mbg) cause cardiac arrhythmias.
3. Pretreatment of the animals with polyclonal antidigoxin rabbit IgG significantly reduces the incidence of arrhythmias and pretreatment with anti-Mbg antibody markedly reduces arrhythmias. We believe this means that antidigoxin IgG and anti-Mbg bind the circulating EDLF and prevent the development of its physiological effects.
4. DIGIBIND, Fab fragments of bovine antidigoxin antibody, even at extremely high concentrations was almost inactive in suppressing the ischemia-induced arrhythmias. Digoxin, therefore, is not the EDLF responsible for causing arrhythmias.

EXAMPLE 6

Human Myocardial Infarction
EDLF in Human AMI

Fifty-four (54) patients who had never taken digitalis drugs and had no known history associated with increased concentrations of EDLF, e.g., severe hypertension, renal or hepatic disease, and endocrine dysfunction, who were admitted to the coronary care unit of the Djanelidze Emergency Medicine Institute with a first time transmural acute myocardial infarction (AMI) were studied. Also not included in the study were patients who received systemic thrombolytic therapy. The diagnosis of AMI was based upon: typical chest pain of at least thirty minutes duration, ST segment elevation on the ECG with subsequent development of Q waves in the involved leads (Minnesota Codes 1-1-1, 1-2-5, 1-2-6, and 1-2-7), and increase of plasma total creatine phosphokinase and lactate dehydrogenase.

Patients known to have unstable angina pectoris, suspected (but not later confirmed) AMI, and healthy donors served as controls.

Venous blood samples were obtained from the patients each day for ten days and on the fourteenth day following the diagnosis of AMI. Blood was collected in cooled polyethylene tubes containing 10 $\mu$M phenylmethylsulfonylfluoride in 0.1 mol/liter EDTA. The mixture was frozen at −18° C. prior to assay. Plasma concentrations of EDLF were measured using the dissociation-enhanced lanthanide fluoroimmunoassay method digoxin kit and expressed as ng/ml of digoxin equivalents. The results were analyzed statistically using student's t-test.

Fifty-four Caucasian patients (47 male, 7 females) ages 39 to 72 years, (mean age 45 years) with AMI, 16 Caucasian male patients with unstable angina pectoris and suspected AMI ranging in age from 40 to 67 years, and eight healthy donors (3 males, 5 females), mean age 39.3 years, were enrolled in the study.

Plasma concentrations of digoxin-like immunoreactivity in patients during the first 24 hours following onset of AMI were significantly increased (1.25±0.26 ng/ml) as compared with the healthy controls (0.34±0.08 ng/ml) and patients with unstable angina pectoris (0.04*14 0.06* ng/ml) . The condition of seven of the patients within the first 24 hours after onset of AMI was complicated by primary ventricular fibrillation. In these patients the concentration of EDLF was significantly higher (2.54±0.67 ng/ml) than in the 47 patients with AMI who did not experience ventricular fibrillation (1.05 0.27 ng/ml), p<0.05). During the first 24-hour period of time, 14 of the patients exhibited manifestations of severe congestive heart failure. In these patients, the concentration of EDLF immunoreactivity was significantly lower (0.32±0.09 ng/ml) than in the other 40 patients with AMI and without congestive heart failure (1.51±0.32 ng/ml).

Between the period of 24–48 hours after onset of AMI the plasma levels of EDLF of the AMI group decreased to levels of the control group (0.26±0.04), and did not differ significantly from the control values during the subsequent two-week period of assay and observation. Commencing after the second day of AMI no significant differences were observed in the plasma concentrations of digoxin-like immunoreactivity between patients with uncomplicated AMI and those with AMI complicated by ventricular fibrillation or congestive heart failure.

The results with the human patients discussed in this example were in agreement with the results obtained in Example 5 demonstrating that plasma concentration of the substances having the property to inhibit Na,K-ATPase is increased in animals exposed to acute coronary ligation. The results of the experimental tests clearly prove the proarrhythmic action of EDLF in AMI and the correlation between plasma levels of EDLF and incidence of ventricular arrhythmias.

Mbg in Human AMI

Eight male patients the first day after the onset of a first MI were studied as above. The peak plasma levels of marinobufagin-like immunoreactivity were 4.30±0.7 $\mu$Moles/l as compared with 1.2±0.2 $\mu$Moles/l in the 6 healthy controls.

Samples of heparinized blood were obtained from 3 male patients during the first 12 hours after the onset of first transmural myocardial infarction. The activity of the ouabain-sensitive Na,K-pump was measured using the known Rubidium (ouabain-inhibitable rubidium uptake) technique. Blood samples of the patients were analyzed in duplicate, in the presence and in the absence of monoclonal antiMbg antibody (100 ug/ml). In the untreated samples, activity of Na,K-pump (ouabain-sensitive Rb uptake by 1 ml of the suspension of erythrocytes) was inhibited by 70%. At the same time, preincubation of the whole blood with antibody for 30 minutes completely restored the activity of the Na,K-pump. Activity of the Na,K-pump in the erythrocytes from 8 healthy controls was unaffected by the pretreatment with antiMbg antibody.

This example demonstrates that the activity of the Na,K-pump in red blood cells in the acute period of myocardial infarction is depressed and that MLIR acts as a marker for acute MI in humans. This observation is in agreement with the previous data showing that activity of Na,K-ATPase in humans with myocardial infarction and in rats with acute myocardial ischemia is inhibited. It is known and has been repeatedly demonstrated that the changes in the membrane of erythrocytes reflect the membrane changes occurring in cardiovascular tissues in various diseases and due to the treatment with different drugs.

EXAMPLE 8

Diagnosis of Hypertension

Adult male Wistar rats (n=6) were subjected to acute plasma volume expansion as described by Gonick et al. Measurements as described above showed a 30% inhibition of the Na,K-pump and a four-fold increase in the level of MLIR. Thus, in this model of hypertension, MLIR was a marker for hypertension.

CONCLUSION

While the invention has been described in detail and with reference to specific embodiments thereof, it is apparent to one skilled in the art that various changes and modifications may be made therein without departing from the spirit of the present invention and therefore, that these descriptions should not be construed as limitations on the scope of the invention, but rather as an exemplification of one preferred embodiment thereof. Accordingly, the scope of the invention should be determined not by the embodiments illustrated, but by the appended claims and their legal equivalents.

REFERENCES 1. de Wardener H W, Clarkson E N Concept of natriuretic hormone, Physiol Rev, 1985, 65, 658–759.
2. Cloix T-F Endogenous digitalis like compounds. A tentative update of chemical and biological studies. Hypertension, 1987, 10 (Suppl. 1), 1-67–1-70.
3. Blaustein M P The cellular basis of cardiotonic steroid action. Trends in Pharmacol Sci, 1985, 6, 289–292.
4. Conick H C, Kramer N J, Paul W, Thu E Circulating inhibitor of sodium-potassium activated adenosine triphosphatase after expansion of extracellular fluid volume in rats, Clin Sci Mol Med, 1977, 53, 329, potassium activated adenosine triphosphatase after expansion of extracellular fluid volume in rats, Clin Sci Mel Med, 1977, 53, 329–344.
5. Hamlyn J M, Ringel R, Schaeffer J, et al., Nature, 1982, 300, 650–652.
6. de The H, Devynak M A, Rosenfeld J., et al., J Cardiovaso Pharmacol, 1984, 6 (Suppl. 1), 5-49–5-51.
7. Kunes J., Stolba P., Pohlova I., et al. , The importance of endogenous digoxin-like factors in rats with various forms of experimental hypertension, Clin Exp Hypertens, 1985, A7, 707–720.
8. Craves S W, The possible role of digitalis-like factors in pregnancy-induced hypertension, Hypertension, 1987, 10, 184–186.
9. Doris P A, Stocco D M An endogenous digitalis-like factor derived from the adrenal gland: studies of adrenal tissue of various sources, Endocrinology, 1989, 125, 2573–2579.
10. Ludens 4.H., Clark M A, DuCharme D W, et al. Purification of an endogonaus digitalis-like factor from human plasma for structural analysis, Hypertension, 1991, 17, 923–929.
11. Flier J H Ouabain-like activity in toad skin and its implications for endogenous regulation of ion transport, Nature, 1978, 27&, 285–286.
12. Schreiber V, Kolbel P, Stepan 4., et al. Digoxin-like immunoreactivity in the serum of rats with cardiac overload, J Mol. Cell Cardiol, 1981., 13, 107–109.
13. Huang C T, and Smith R M Lowering of blood pressure in chronic aortic coarotate hypertensive rats with antidigoxin antiserum, Life Sci, 1984, 33, 113–118.
14. Clough D L, Pamnani M B, Haddy P S Myocardial Na,K-ATPase activity in rats with steroid and spontaneous hypertension, J Hypertension, 1984, 2, 141–148.
15. Fogoo M, and Godfraind T Interaction of cardiodigin, endogenous inhibitor of Na,K-ATPase with antidigoxin antibodies, Biochem Biophys Res Commun, 1985, 129, 553–559.
16. de Pover A Endogenous digitalis-like factor and inotropic receptor sites in the heart, Europ J. Pharmacol, 1984, 36, 365–366.
17. Navaratnam S, Chau T, Agbanyo M , et al. Positive inotropic effect of porcine left ventricular extract on canine ventricular muscle, Brit J Pharmacol, 1990, 101, 370–374.
18. Maixent J-M, and Lelievre L G Differential inactivation of inotropic and toxic digitalis receptors in ischemic dog heart, J Biol Chem, 1987, 262, 12458–12462.
19. Bagrov A Y, Ganelina I E, Nikiforova K A, et al. Antifibrillatory effect of antidigoxin antibodies in experimental myocardial infarction (in Russian) in Diagnosis and treatment of myocardial infarction, Tbilisi, Metsnierba Eds, 1987, 177–179.
20. Bagrev A Y, Fedorova O V, Maslova M N, et al—Antiarrhythmic effect of antidigoxin antibodies in acute myocardial isahemia in rats, Europ J Pharmacol, 1989, 162, 195–196.
21. Bagrov A Y (Abstract). Endogenous digoxin-like factor; possible emergency implications, Prehosp Disaster med, 1990, 5, 186.
22. Bagrov A Y, Fedorova O V, Maslova M N et al., Endogenous digoxin-like factor (EDLF) in acute myocardial infarction (AMI), J Mol Cell Cardiol, 1990.
23. Bagrov A Y, Fedorova O V, Maslova M N, et al., Endogenous plasma Na,K-ATPase inhibitory activity and digoxin-like immunoreactivity after acute myocardial infarction, Cardiovasc Res, 1991a, 25, 371–377.
24. Bagrov A Y, Fedorova O V, Roukoyatkina N I, and Zhabko E P, Evidence for arrhythmogenic action of endogenous digoxin-like factor in acute myocardial ischemia, Europ Heart J. 1991b, 12 (Suppl.) , p. 323.
25. Delva P, Devyrck M-A, Degan M, et al., Correlation between plasma level of an endogenous digitalis-like substance and haemodynamic parameters measured during cardiac catheterization, J. Hypertension, 1988, 6 (Suppl. 4), S-348–S-350
26. Clark O, Foreman M I, Kane K A, et al. Coronary artery ligation in anesthetized rat as a method for the production of experimental disrhythmias and for the determination of infarct size, J Pharmacol Methods, 1980, 3, 357–368.
27. Curd J, Smith T W, Jaton J-C, Haber E, The isolation of digoxin-specific antibody and its use in reversing the effect of digoxin, Proc Natl Acad Sci USA, 1971, 68, 2401–2406.
28. Mir K A, Morgan K, Lewis M, et al. Problems and pitfalls in the isolation of an endogenous Na,K-ATPase inhibitor, Hypertension, 1987, 10 (Suppl. 1), 1–57-1–61.
29. Bova S, Blaustein M P, Ludens J H et al., Effects of an endogenous ouabain-like compound on heart and aorta, Hypertension, 1991, 17, 944–950.
30. Cress L W, Ereas W, Haddy P, and Muldoon S, Effects of bufalin on norepinephrine turnover in canine saphenous vein, Hypertension, 1991, 18, 516–522.

31. Meyer K, Linde H, Collection of toad venoms and chemistry of toad venom steroids in Bucheri W, and Buckley E (Eds), Venomous animals and their venoms, Academic Press, New York, 1971, 521–561.
32. Barbier M, Schroler H, Meyer K, et al,. Helvetica Chimica Acta, 1959, Ed. 42, 2486–2505.
33. Shimada K, Fujii Y, Yamashita E, et al., Studies on cardiotonic steroids from the skin of Japanese toad, Chem Pharm Bull, 1977, 25, 714–730.
34. Zelnik R, Ziti L M, Thin layer chromatography chromatoplate analysis of the bufadienolides isolated from toad venoms, J Chromatoghaphy, 1962, 9, 371–373.
35. McKinney M M, and Parkison A, A simple non-chromatographic procedure to purify immunoglobulins from serum and ascites fluid, J. Immunol Methods, 1987, 96, 271–278.
36. Goodlin R C, Antidigoxin antibodies in eclampsia, New Engl J Med, 1988, Vol. 318, p. 518–519.
37. Naomi S, Craves S, Lazarus M, Williams G H, Hollenberg N K, Variation in apparent serum digitalis-like factor levels with different digoxin antibodies, Am J Hypertension, 1991, 4, p. 795–801.
38. Goto A, Yamada K, Ishii M, Sugimoto T, Yoshioka M, Immunoreactivity of endogenous digitalis-like factors, Biochem Pharmacol, 1991, 41, p. 1261–1263.
39. Yamahara J, Tanaka S, Matsuda D, Sawada T, Fujimura H, The mode action of cardiotonic steroids isolated from Toad cake in perfused working guinea pig heart and effect of cinobufagin on experimental heart failure, Nippon Yakurigak Zasshi, 1986, 88, p. 413–423.
40. Chen K K and Kovarikova A, Pharmacology and Toxicology of Toad Venom, J Pharm S C Vol 56 No. 12, December, 1967.
41. Shimada K, Ohishi K, Fukunaga H, Ro J and Nambara T, Structural-Activity Relationship of Bufatoxins and Related compounds For the Inhibition of Na+, K+-Adenosine Triphosphatase, J Pharmacobio-Dyn., 8, 1054–1059 (1985).
42. Johnston K M, MacLeod B A, Walker M J A, Responses to Ligation Of A Coronary Artery In Conscious Rats and The Actions Of Arrythmias, Department of Pharmacology, Faculty of Medicine, Univ. of British Columbia, Received, Feb. 3, 1983.
43. U.S. Pat. No. 5,164,296, Blaustein et al "Assay Methods Involving Ouabain".
44. Koenigs E, Knorr E, Uber einige Derivate des Traubenzuskers und der Galactose. *Ber Deut Chem Ges* 1901; 34:
45. Wulf G, Kruger W, Die Umzetzung vin a-Acetobromglukose mit den Silbersalzen Hydroxycarbonsauren. *Chem Ber* 1971; 104: 1387–1298.
46. Helsingius P, Hemmila I, Lovgren T, Solid phase immunoassay of digoxin by measuring time resolved fluorescence. *Clin Chem* 1986; 32: 1767–1769.

I claim:

1. A method for determining whether a human is suffering from myocardial infarction, comprising the steps of
   (a) obtaining plasma from a human suspected of having a myocardial infarction;
   (b) measuring, by immunoassay with antibodies specific for marinobufagin, the level of immunoreactivity with said antibodies in the plasma obtained in step (a);
   (c) comparing the level of immunoreactivity with antibodies specific for marinobufagin obtained in step (b) with a standard level of immunoreactivity with antibodies specific for marinobufagin, wherein a elevated level of immunoreactivity in said human compared to the standard is an indication that the human is experiencing a myocardial infarction.

2. The method of claim 1, wherein said antibodies are polyclonal antibodies.

3. A method for measuring in a human endogenous digoxin-like factors that are immunoreactive with antimarinobufagin antibodies, comprising the steps of:
   (a) obtaining plasma from a human;
   (b) measuring, by immunoassay with antibodies specific for marinobufagin, the level of immunoreactivity with said antibodies in the plasma obtained in step (a);
   (c) comparing the level of immunoreactivity with antibodies specific for marinobufagin obtained in step (b) with a standard level of immunoreactivity with antibodies specific for marinobufagin.

4. The method of claim 3, wherein said antibodies are polyclonal antibodies.

* * * * *